US00PP37594P2

(12) United States Plant Patent
Byrne et al.

(10) Patent No.: US PP37,594 P2
(45) Date of Patent: Aug. 18, 2026

(54) PEACH TREE NAMED 'TRH2E122W'

(50) Latin Name: *Prunus persica.*
Varietal Denomination: TRH2E122W

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/295,148

(22) Filed: Aug. 8, 2025

(51) Int. Cl.
*A01H 5/08* (2018.01)
*A01H 6/74* (2018.01)

(52) U.S. Cl.
USPC ..... Plt./196

(58) Field of Classification Search
USPC ..... Plt./196
CPC ..... A01H 5/08; A01H 5/00; A01H 6/7463; A01H 6/74; A01H 6/7427
See application file for complete search history.

(56) References Cited

U.S. PATENT DOCUMENTS

| | | | | |
|---|---|---|---|---|
| PP14,627 | P3 * | 3/2004 | Byrne | A01H 5/08 Plt./197 |
| PP14,629 | P3 | 3/2004 | Byrne et al. | |
| PP26,119 | P3 | 11/2015 | Byrne et al. | |
| PP30,123 | P3 * | 1/2019 | Goffreda | A01H 6/7454 Plt./188 |
| 2016/0205832 | P1 * | 7/2016 | Byrne | Plt./195 |
| 2016/0205836 | P1 * | 7/2016 | Byrne | Plt./196 |

OTHER PUBLICATIONS

Byrne and Anderson, 2013. White Delight peach series: Four medium-chill, subacid, white- fleshed peaches. HortScience 48(8): 1056-1058.

* cited by examiner

*Primary Examiner* — June Hwu
(74) *Attorney, Agent, or Firm* — Dentons US LLP

(57) ABSTRACT

Disclosed is a new variety of *Prunus persica* named 'TRH2E122W'. This new variety, which requires approximately 450 chilling units of dormancy, is considered to be a peach tree of carly midseason maturity, which produces acid-sweet, firm, freestone, white-fleshed peach with abundant red coloration in the flesh and on the skin that is suitable for fresh fruit market.

5 Drawing Sheets

Latin name of the genus and species of the plant claimed: *Prunus persica.*

Variety denomination: 'TRH2E122W'.

BACKGROUND OF THE INVENTION

This invention relates to a peach tree and, more specifically, to a peach tree referred to as a variety of *Prunus persica* named 'TRH2E122W', which requires approximately 450 chilling units of dormancy, matures in the early midseason and produces a firm freestone, white-flesh, acid-sweet peach that develops an abundance of red pigment in the flesh upon ripening. The present peach tree was the result of an ongoing Stone Fruit Breeding Program in College Station, Brazos County, Texas. To this end, controlled crosses were made each year to produce seedling populations from which improved progenies are evaluated and selected. The seedling 'TRH2E122W' was derived from a cross between a medium-chill, white-flesh, subacid, peach 'White Delight Two' (not patented, U.S. Plant Patent Application Publication 2016/0205832 P1, (abandoned); Byrne and Anderson, 2013. White Delight peach series: Four medium-chill, subacid, white-fleshed peaches. HortScience 48(8):1056-1058) and a low-chill acid-sweet, yellow-fleshed peach, 'TexFirst' (U.S. Plant Pat. No. 26,119; Byrne and Anderson, 2012. TexFirst, an early-ripening, low-chill peach for the subtropics. HortScience 47(12): 1803-1804).

Resulting seed from the cross between 'White Delight Two' and 'TexFirst' were planted in 2011 in an experimental plot in Floresville, TX. 'TRH2E122W' was marked for subsequent observation in 2013 and noted as having exceptional characteristics.

'TRH2E122W' was bud grafted onto virus-free Nemaguard (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2023), Somerville (2016-2023) and Fairfield (2013-2020), Texas. This evaluation clearly demonstrated that the re-propagated trees were true to the characteristics of the original seedling in all observable aspects.

SUMMARY OF THE INVENTION

The 'TRH2E122W' peach is characterized as noteworthy by producing freestone white-flesh fruit that develops abundant red coloration upon ripening that ripens in the early midseason; is considered firm and has a 60-80% red blush over a light-yellow ground color. In this regard, the present variety of peach tree bears fruit that are ripe for commercial harvesting and shipment in early to mid-June, when the fruit is grown in the medium chill zone of Texas. 'TRH2E122W' blooms 2 weeks before its female parent 'White Delight Two' and ~ 12 days after its pollen parent 'TexFirst'. It ripens ~5 days after its female parent and 6 weeks after its pollen parent. 'TRH2E122W' differs from its white-fleshed, subacid, peach female parent as it has acid flesh and differs from its yellow-fleshed, acid-sweet pollen parent as it is a white-flesh peach. This new acid-sweet, white-flesh peach with abundant red coloration in the flesh upon ripening exhibits potential to be commercialized in regions that have chilling requirements that are relatively low.

'TRH2E122W' differs from the commercial cultivar 'White Zest One' (not patented, U.S. Plant Patent Application Publication 2016/0205836 P1, abandoned) in that the anthocyanin accumulation within the flesh is much lower (20-30% vs. 70-80%), it has showy blooms as compared to non showy blooms, it has reniform rather than globose glands, requires 100 more chilling hours to break dormancy (550 vs 450 chill hours), blooms a week later (February 22 vs February 15), ripens a week earlier and has a ~12 day shorter fruit development period than does 'TRH2E122W'.

'TRH2E122W' differs from the commercial cultivar 'White Delight Two' in that it has less flesh anthocyanin accumulation (10-20% vs. 70-80%), has subacid rather than acid flesh, requires 100 more chilling hours to break dormancy (550 vs 450 chill hours), blooms 2 weeks later (March 1$^{st}$ vs February 15$^{th}$), ripens ~ 5 days earlier and has a ~16 day shorter fruit development period than does 'TRH2E122W'.

'TRH2E122W' differs from other selections, including 'TRH2B102LW' (claimed in U.S. Ser. No. 19/336,385), 'TRH2C108W' (claimed in U.S. Ser. No. 19/336,380) and 'TRH3C114W' (claimed in U.S. Ser. No. 19/336,169) derived from the same parents as they have less anthocyanin accumulation in the flesh (10-25% vs. 70-80%), have reniform leaf glands rather than globose leaf glands, ripen earlier (May 20-28 vs June 11) and have a lower fruit development period (80-96 days vs 112 days) than does 'TRH2E122W'.

BRIEF DESCRIPTION OF THE DRAWINGS

This new variety of peach tree is illustrated by the accompanying photographs of plants in their 5$^{th}$ year grown in Pleasanton, Texas, as provided in FIGS. 1-5.

These photographs show the plant's typical fruit, foliage, and flowers, and the colors shown are as true as can be reasonably obtained by conventional photographic procedures.

DETAILED BOTANICAL DESCRIPTION

Figure 1:
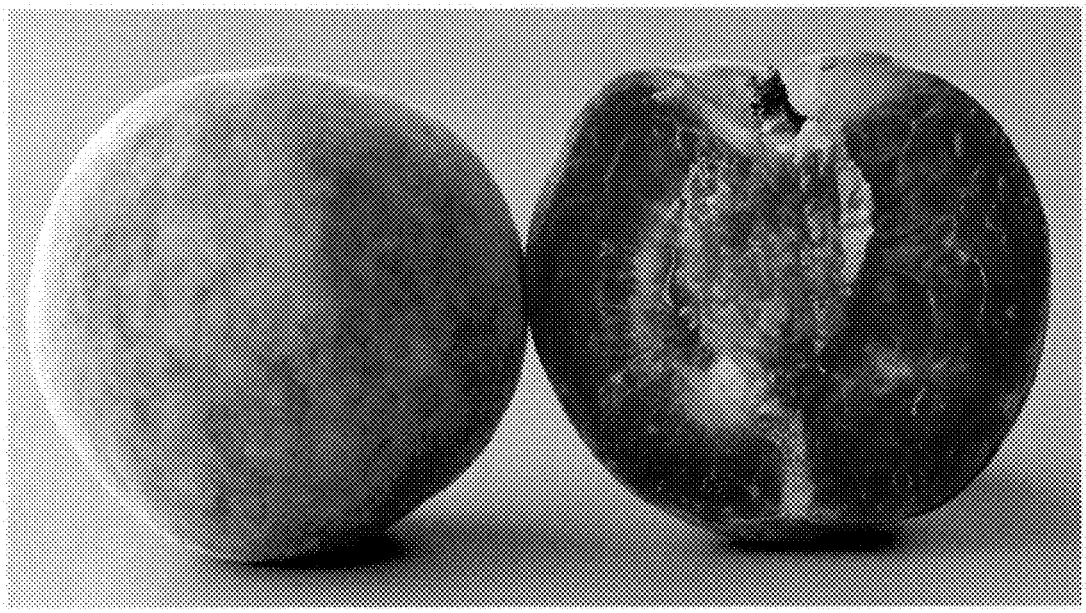
FIG. 1—Fruit of 'TRH2E122W' produced in Pleasanton, Texas showing external and internal coloration.
Figure 2:
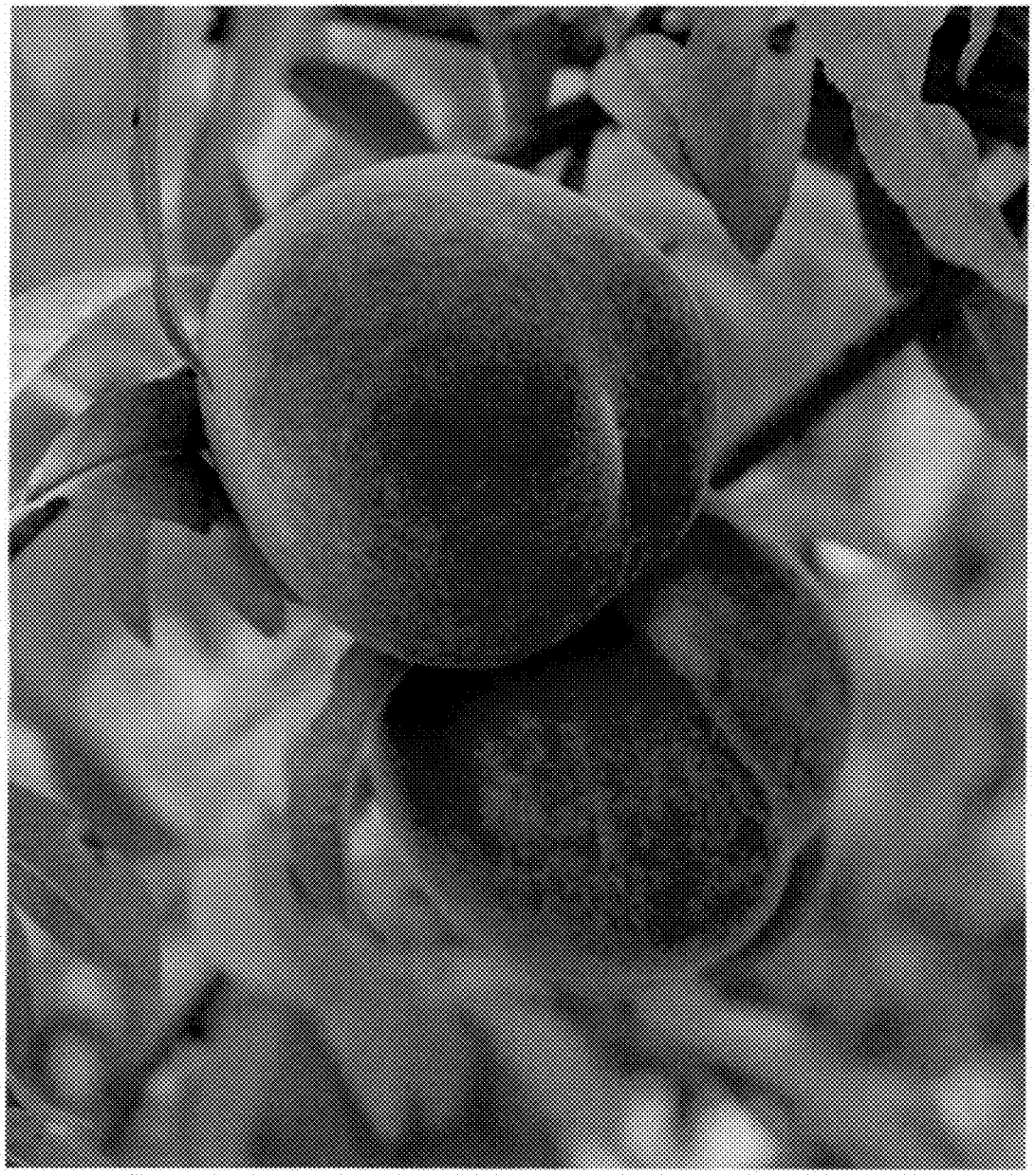
FIG. 2—'TRH2E122W' fruit produced in Pleasanton, Texas showing shape and external coloration.
Figure 3:
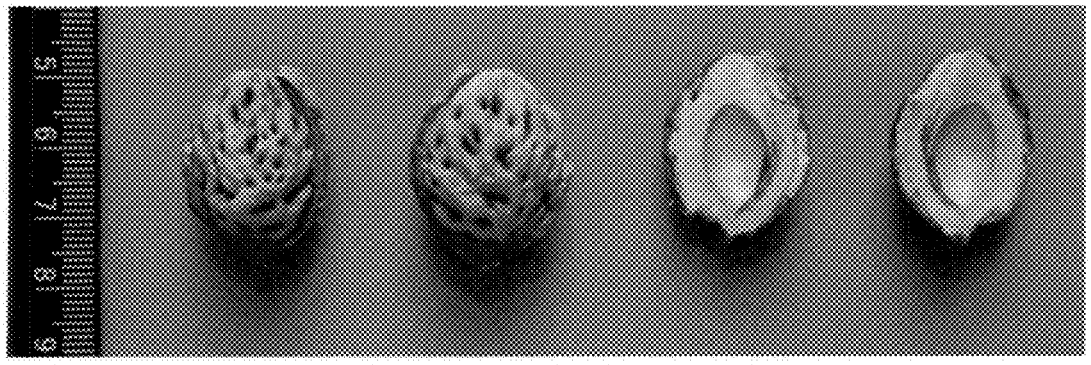
FIG. 3—Photograph of the endocarps of the 'TRH2E122W' peach. The ruler is in centimeters.
Figure 4:
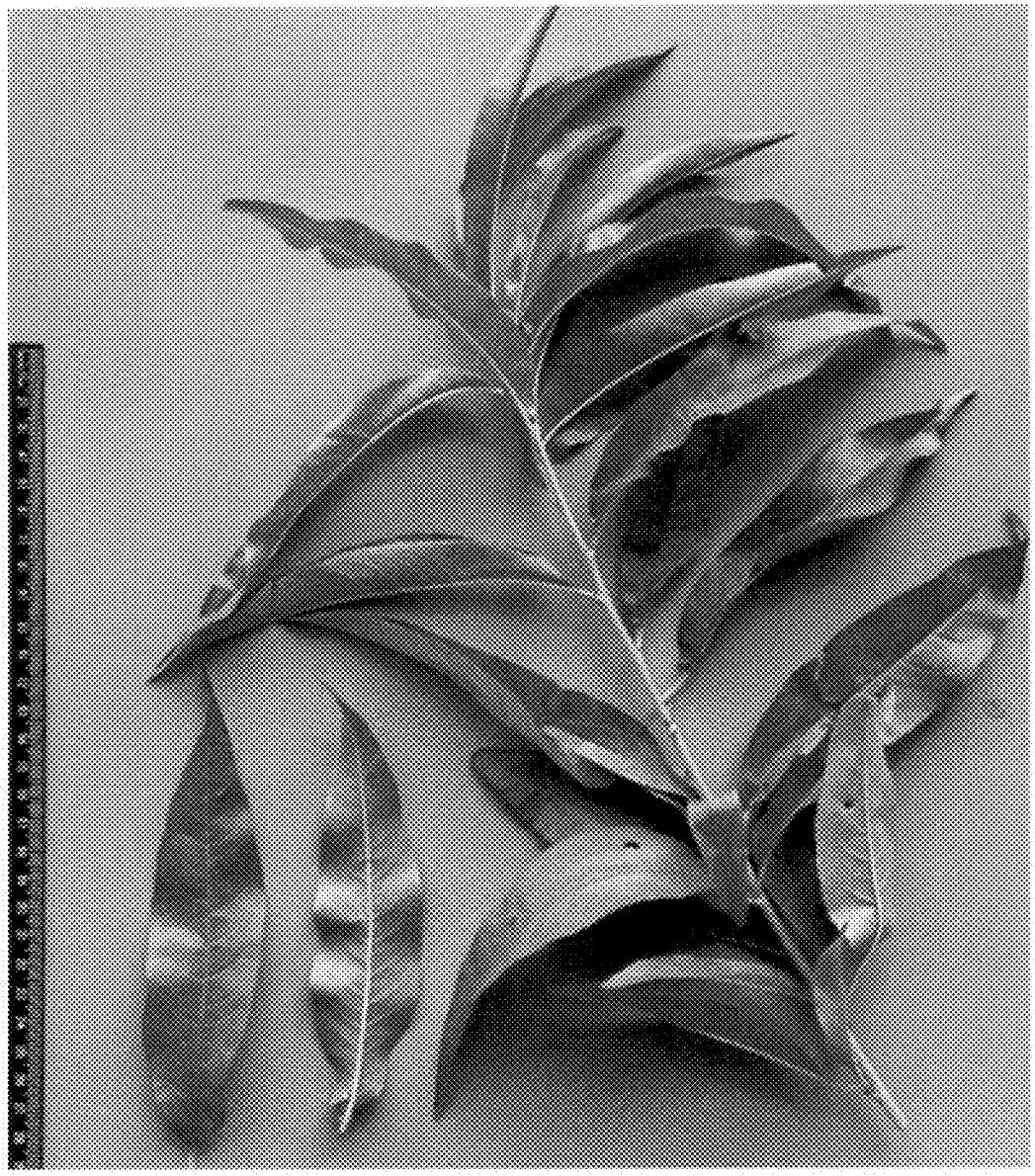
FIG. 4—A stem showing the leaves of the 'TRH2E122W' peach. The ruler is in centimeters.
Figure 5:
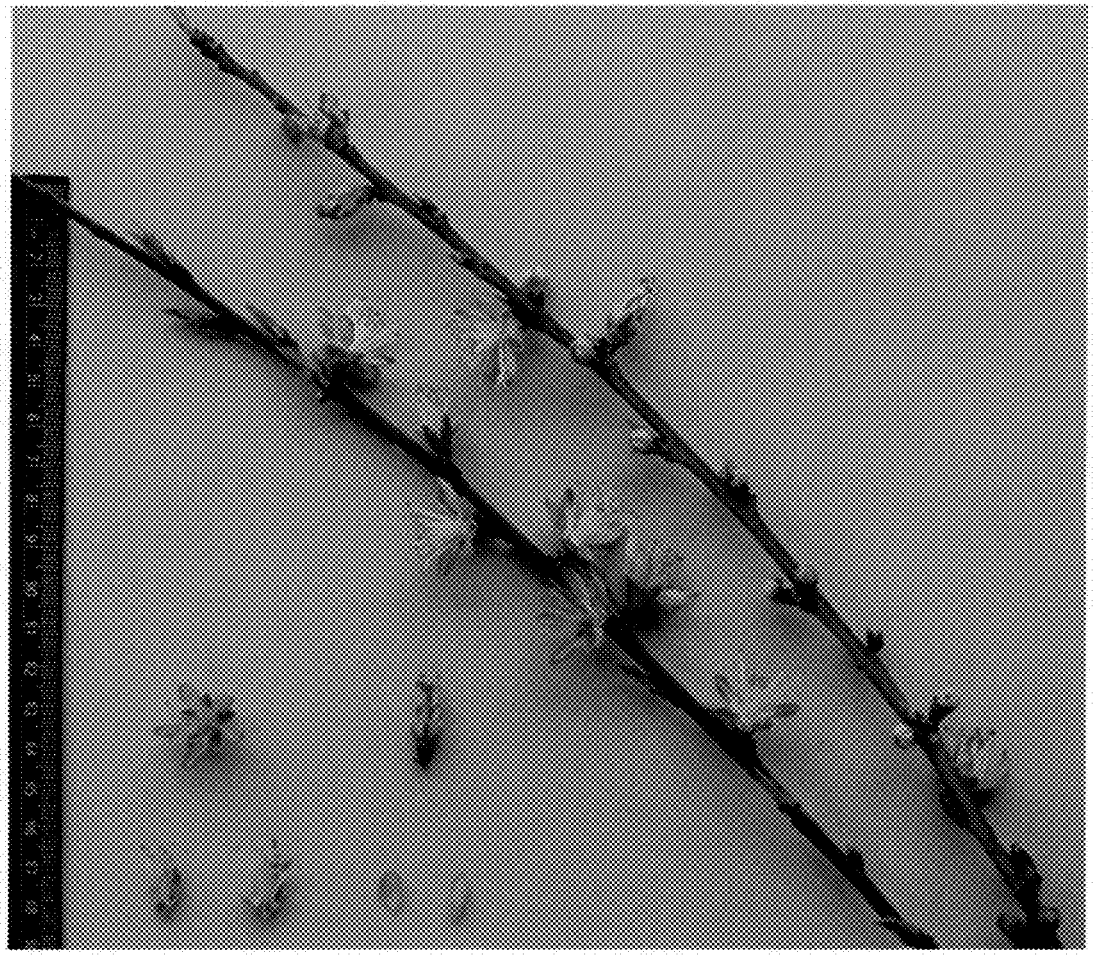
FIG. 5—A stem showing the flowers of the 'TRH2E122W' peach. The ruler is in centimeters.

Referring more specifically to the pomological details of this new and distinct variety of peach tree, the following has been observed under the ecological conditions prevailing at the experimental orchards in the medium chill zone of Texas (Pleasanton, Fairfield and Somerville). All major color code designations are by reference to the RHS Colour Chart (2001 Edition) or the RHS Mini Colour Chart (2005) provided by The Royal Horticultural Society of Great Britain. Colors are approximate as color depends on horticultural practices such as light level and fertilization rate, among others.

Tree:

*Size.*—Generally average to above average as compared to other common peach cultivars grown in the medium chill zone of Texas.

*Height.*—8 to 9 feet (2.4 to 2.7 m) at the end of the 2024 growing season.

*Width.*—9 feet width (2.7 m) at the end of the 2024 growing season.

*Productivity.*—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape.*—The 'TRH2E122W' peach has been trained in an open center configuration and exhibits a semi spreading growth type as seen in peach varieties 'Texprince' (U.S. Plant Pat. No. 14,629; Byrne, D. H. and T. A. Bacon. 2004. TexPrince, a mid-season medium chill peach. HortScience 39(3):631-632) and 'Texking' (U.S. Plant Pat. No. 14,627; Byrne, D. H. and T. A. Bacon. 2004. TexKing, an early ripening medium chill peach. HortScience 39:442-443).

*Current season growth.*—The current season growth for the new variety was approximately 1.5 to 3.5 feet (0.45-1.1 m). Vigor is medium to medium high compared to other common peach varieties grown in the medium chill zone of Texas.

*Regularity of bearing.*—Regular in the absence of temperatures of 28° F. or lower during bloom and considered hardy in the medium chill zone of Texas.

Trunk:

*Size.*—Approximately 2.5 inches (6.4 cm) in diameter and 9 inches (22.9 cm) in circumference when measured at a distance of approximately 12 inches (30.5 cm) above the soil level, at the end of the 2024 growing season on a three-year old tree.

*Bark texture.*—Considered moderately rough with numerous folds of papery scarf-like skin being present.

*Bark coloration.*—Variable, colors (RHS2001) present are 156D of the Greyed-White Group, 157A of the Green-White Group, 164A, 165B, 166B, 175A, 175B, 176A and 176B of the Greyed-Orange Group, N200C and N200D of the Brown Group and 201D of the Grey Group.

Branches:

*Thickness.*—Average (about 3.2 to 3.5 cm in diameter as measured 10 cm from the trunk on a three-year old tree) as compared to other varieties.

*Surface texture.*—Average and appearing furrowed on wood that is several years old.

*Lenticels.*—Flat, oval lenticels present. The lenticels range in size from approximately 5 to 9 mm in width and were approximately 2 mm in height with a density of 1.0 lenticels per square centimeter.

*Current season shoots.*—Surface texture-Substantially glabrous.

*Internode length.*—Approximately 18 to 22 mm as measured in the middle of a current season stem.

*Color of mature branches.*—The predominant colors (RHS2001) are 165A, 166A, 175A and 177A of the Greyed-Orange Group, 200B, 200C, 200D and N200D of the Brown Group and 201D of the Grey Group.

*Current season shoots.*—Color (RHS2001)— Light to medium green, 144A, 146B, 146C and 146D of Yellow-Green Group, with some reddish-brown coloration appearing on exposed surface of the shoots (165A and 166A of the Greyed-Orange Group and N199B and N199C of the Grey-Brown Group).

Leaves:

*Size.*—Considered moderately small for the species. Leaf measurements have been taken from vigorous upright current season growth approximately at mid-shoot.

*Leaf length.*—Approximately 126 to 135 mm.

*Leaf width.*—Approximately 26 to 30 mm.

*Leaf thickness.*—Less than 1 mm.

*Leaf form.*—Lanceolate.

*Leaf tip form.*—Acuminate.

*Leaf upper surface color* (*RHS*2001).—Green, 137A and 137B of the Green Group.

*Leaf lower surface color* (*RHS*2001).—Green varying among 138B of the Green Group and 146A and 146B of the Yellow-Green Group.

*Leaf lower mid-vein color* (*RHS*2001).—Light yellow green, 145C and 145D of the Yellow-Green Group.

*Leaf margins.*—Form — Considered crenate. Uniformity — Considered generally uniform.

*Leaf petioles.*—Size— Considered medium long. Length — Approximately 10 to 12 mm. Thickness — Approximately 1 to 1.5 mm. Color (RHS2001) — Pale green, N144D, 145A and 145B of the Yellow-Green Group.

*Leaf glands.*—Size — Approximately 1 mm in height and less than 1 mm in width. Number — Generally 0-2 per leaf. Type— Reniform. Color (RHS2001) — Greenish brown, 166A and 177A of the Greyed-Orange Group, N199B of the Grey-Brown Group and 200B and 200C of the Brown Group.

*Leaf stipules.*—Size — Medium to medium large for the species. Length — Approximately 10 to 14 mm. Form — Lanceolate. Color (RHS2001) The abaxial/adaxial color is Green, 144A, N144C, 146B, 146C and 146D of the Yellow-Green Group. The stipules are early deciduous.

*Ratio of flower buds to vegetative buds.*—Generally has 2 flower buds per vegetative bud.

Flowers:

*Floral buds.*—General — The floral buds are conic in form, and slightly appressed relative to the bearing shoot. Color — Mature buds are brown, (approximately 155A, 166A and 175A of the Greyed-Orange Group and 200C of the Brown Group). The buds are considered hardy when grown in the medium chill zone of Texas. Mature Bud Length — 3 to 5 mm. Mature Bud Width — 1 to 2 mm. Bud Length — Approximately 9 to 19 mm.

*Blooming type.*—Mean date of full bloom in the medium chill zone of Texas was in mid-February (Feb 16th at Somerville and Fairfield experimental plots), a few days before or with the commercial cultivars 'Texking' and 'Flordaking' (not patented; Andrews, C.P. 1979. 'Flordaking' peach. HortScience 14(1):81-82).

*Flower type.*—Non-showy.

*Flower size.*—Flower diameter at full bloom is approximately 22 to 27 mm.

*Bloom quantity.*—Considered abundant.

*Flower bud frequency.*—Normally 1 to 2 per node.

*Petal Size.*—General — Considered medium for the species. Width — Approximately 7 to 8 mm. Length — Approximately 11 to 13 mm.

*Petal form.*—Ovate.

*Petal count.*—Nearly always 5.

*Petal color* (*RHS*2001) *upper/lower surface.*—Medium to dark pink when young (62B, 62C, 63A, 63B, 63C, 63D, 65A, N66A, N66B and 68B of the Red-Purple Group), becoming darker with advanced senescence.

*Petal claw.*—Form — The claw is considered truncate in shape. Length — Approximately 1 mm. Width — Approximately 1 mm.

*Petal margins.*—Generally considered variable, from nearly smooth to slightly undulate.

*Petal apex.*—Generally— The petal apices appear slightly domed.

*Flower pedicel.*—Length— Considered moderately short, and having an average length of approximately 1to 2 mm. Thickness — Approximately 1 mm. Color (RHS2001) — A light green (N144B, 145B and 145C of the Yellow-Green Group).

*Floral nectaries.*—Color (RHS2001) — Light to medium yellow (7A, 7B, 7C, 7D, 9A, 9B, 9C and 13C of the Yellow Group and 14C, 15A, 15B, 15C, 16B and 16C of the Yellow-Orange Group).

*Sepals.*—Sepal count — Generally 5 sepals per flower. Surface Texture — The surface has a short, fine, wooly texture. Size — Width approximately 3 mm, Height 5-6 mm. Sepal Form — Ovate Lower Sepal Color (RHS2001)— Maroon and green with white (approximately 58A, 59C, 60A, 60B, 60C and 63A of the Red-Purple Group; 144B, N144C and N144D of the Yellow-Green Group; 155A, 155B, 155C, 155D of the White Group and 185A, 185B, 187C and 187D of the Greyed-Purple Group).

*Floral cup* (*hypanthium*).—Surface Texture— Generally glabrous. Color (RHS2001) — Maroon with green (approximately 58A, 59C, 60A, 60B, 60C and 63A of the Red-Purple Group; 144B, N144C and N144D of the Yellow-Green Group and 185A, 185B, 187C and 187D of the Greyed-Purple Group).

*Anthers.*—General — Average (1 mm or less in length) in size for the species. Color (RHS2001) — Medium to dark orange (approximately 28A of the Orange Group, and 31A. 31B, 32A, 34A and 34B of the Orange-Red Group).

*Pollen production.*—Pollen is abundant and is a orangish-yellow color (approximately RHS2001 16A, 16B, 17A, 17B and 17C of the Yellow-Orange Group, 25A, N25A and 28A of the Orange Group, 31A, 32A, 32B, 33A, 33B, 33C and 35A of the Orange-Red Group and 169A, 169B and 170A of the Greyed-Orange Group).

*Filaments.*—Size — Variable in length, approximately 9 to 13 mm, with the filaments shorter than the pistil and equal to or longer than the petals at the pink bud stage of flower development. Color (RHS2001)—White (approximately 155A, 155B, 155C and 155D of the White Group) and darkening with advanced maturity.

*Pistil.*—General — Generally taller than the anther height and taller than the petal height at the pink bud stage of development. Length — Approximately 13 to 17 mm, including the ovary. Color (RHS2001) — Considered white with light green when young (approximately 1C, 1D, 2C and 2D of the Green-Yellow Group and 155A, 155B, 155C and 155D of the White Group), and becoming slightly darker with advancing senescence.

*Surface Texture.*—The variety has a pubescent style and ovary.

Fruit:

*Maturity when described.*—The present variety of fruit is described, as it would be found in its firm ripe condition at full commercial maturity. Under the ecological conditions prevailing in the medium chill zone of Texas it would be ripe in early to mid-June. The average ripe date was June 11$^{th}$, June 6$^{th}$, and June 16$^{th}$ at Pleasanton, College Station and Fairfield respectively.

*Size.*—General-Medium large to large for the season and considered uniform. Average Cheek Diameter — Approximately 60 to 67 mm Average Suture Diameter — Approximately 63 to 66 mm Average Axial Diameter — Approximately 59 to 62 mm

*Fruit form.*—Generally considered oblate with unequal halves. Occasionally the fruit exhibits less symmetry when comparing the suture height with the line opposite the suture. The fruit generally exhibits a slightly bulging suture when viewed from the apical aspect.

*Fruit suture.*—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — The suture normally has the same color as the underlying blush plus darker tones, represented by Orange-Red Group N34A, Red Groups 46A and 53A, Red- Purple Group 59A and 59B and Greyed-Purple Group 187A, 187B.

*Ventral surface.*—Form— Considered uniform.

*Stem cavity.*—Width — Approximately 12 to 18 mm Length — Approximately 17 to 21 mm Depth — Approximately 6 to 8 mm

*Fruit base.*—Generally considered flat.

*Fruit apex.*—Generally considered flat without a mucronate tip.

*Fruit stem.*—Length — Approximately 7 mm Thickness — Approximately 3 mm Color (RHS2001) — Light to medium green, 145A, 145B, 145C of the Yellow-Green Group.

*Fruit skin.*—Generally considered medium or average in thickness. Surface Texture — Light, short pubescence. Skin Acidity— Considered neutral. Tenacious to Flesh — Yes at commercial maturity. Tendency to Crack — Not observed. Skin Color — Generally — Variable, with a medium to large amount (approximately 60-80%) of the fruit surface covered with a red blush. Blush Color (RHS2001 — The blush color is considered a medium to dark red (Red Groups 46A, 47A, 47B, 47C, 48A, 53A and 53B, Red-Purple Groups 59A, 59B and 60A and Greyed-Purple Group 18A) and has many degrees of shading and blending occurring between the stated colorations. The fruit skin over color pattern varies from mottled to marbled.

*Skin ground color* (*RHS*2001).—The skin ground color is pale to medium yellow (Yellow Groups 3D, 4C, 4D, 5D, 6D, 8C, 9D, 10C, 10D, 11C, 12D, 13D and 14D and Yellow-Orange Group 18A).

*Flesh color.*—Generally considered white (RHS2005 White Group N999D) with medium to dark pink as it nears the stone cavity with flecks throughout (RHS2001 Red Group 53A, 53B, 53C, Red-Purple Groups 59A, 59B, 60A and 60B and Greyed-Purple Group 187A, 187B). The fruit flesh anthocyanin is strong throughout the fruit from under the skin, centrally in the flesh and around the stone.

*Flesh fibers.*—Fibers are present throughout the flesh.

*Stone cavity color* (*RHS*2001).—Generally considered a medium to dark pink (Red-Purple Groups 59B, 59C, 60A, 60B and 63A).

*Flesh texture.*—Generally, the flesh is considered firm at commercial maturity.

*Ripening.*—Generally the fruit of the present variety ripens evenly.

*Flavor.*—Considered sweet (12-14 Brix) with an acidic flavor.

Stone:

*Attachment.*—Freestone at commercial maturity.

*Stone size.*—Generally considered moderately large relative to the ratio of stone to fruit size. Length — Approximately 35 to 36 mm Width — Approximately 22 to 25 mm Thickness — Approximately 17 to 20 mm

*Fibers.*—Generally a few short fibers are attached sporadically along the surface of the stone.

*Stone form.*—Elliptical

*Stone base.*—The stone is medium to wide.

*Base angle.*—The base angle of the stone is variable, but most frequently is considered slightly oblique to the stone axis.

*Hilium.*—The hilium is approximately 3 to 6 mm long and less than 1 mm wide.

*Apex shape.*—The stone apex shape is considered variable, from medium to wide.

*Stone shape.*—The stone shape is considered elongated.

*Stone surface.*—Surface Texture. — The stone surface texture consists of single pits, rosettes of pits and pit chains. Ridges — Numerous fine ridges are present basally and converge towards the base of the stone.

*Ventral edge.*—Considered medium.

*Dorsal edge.*—Shape— Grooved and having moderately rough edges.

*Stone color* (*RHS*2001).—The color of the fresh stone is dark brown with medium pink (Red-and Purple Groups N57A, 58A and 58B, Greyed-Orange Groups 165A, 166A, 177A and 177B Greyed-Brown Group 199B). The color of the inside surface of the endocarp is primarily Greyed-Orange Groups 164B, 165B and 165C and Greyed-Brown Group N199D.

*Tendency to split.*—Has not been observed.

*Kernel.*—The kernel fills the endocarp at harvest and measures approximately 5-6 mm in thickness, 9-11 mm in width, and 16-17 mm in length. When dried the shriveled kernels measure approximately 4 mm in thickness, 9-10 mm in width, and 15-17 mm in length. The colors (RHS2001) of the fresh kernels are primarily Greyed-Orange Groups 164A, 164B, 164C, 165B and 165C.

*Use.*—The subject variety, 'TRH2E122W', is considered to be a peach tree of early-midseason maturity, which produces sweet-acidic, freestone, white-fleshed fruit with abundant red coloration in the flesh which are firm with a 60-80% red blush over a light-yellow ground color and which are useful for the fresh fruit market.

*Keeping quality.*—Retains firmness and flavor after 14 days of refrigeration at 4-5° C.

*Resistance to insects and disease.*—No atypical resistances/susceptibilities were noted under normal cultural practices to date.

*Shipping quality.*—Fruit does not develop internal breakdown and retains good firmness and eating quality after 14 days of refrigeration at 4-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

The invention claimed is:

1. A new and distinct variety of peach tree named 'TRH2E122W', as illustrated and described herein.

* * * * *